United States Patent
Larin et al.

(10) Patent No.: US 10,405,740 B2
(45) Date of Patent: Sep. 10, 2019

(54) OPTICAL COHERENCE ELASTOGRAPHY TO ASSESS BIOMECHANICS AND DETECT PROGRESSION OF OCULAR AND OTHER TISSUES DEGENERATIVE DISEASES

(71) Applicant: University of Houston System, Houston, TX (US)

(72) Inventors: Kirill V. Larin, Friendswood, TX (US); Jiasong Li, Houston, TX (US); Manmohan Singh, Houston, TX (US); Chen Wu, Houston, TX (US); Salavat Aglyamov, Austin, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 8 days.

(21) Appl. No.: 15/632,657

(22) Filed: Jun. 26, 2017

(65) Prior Publication Data
US 2017/0290503 A1  Oct. 12, 2017

Related U.S. Application Data

(63) Continuation of application No. 14/934,663, filed on Nov. 6, 2015, now Pat. No. 9,687,145.
(Continued)

(51) Int. Cl.
*A61B 3/00* (2006.01)
*A61B 3/16* (2006.01)
(Continued)

(52) U.S. Cl.
CPC ............ *A61B 3/0025* (2013.01); *A61B 3/102* (2013.01); *A61B 3/16* (2013.01); *A61B 3/165* (2013.01);
(Continued)

(58) Field of Classification Search
CPC ...... A61B 3/0025; A61B 3/102; A61B 5/0066; A61B 8/485; A61B 8/10; A61B 3/165; A61B 2576/00
See application file for complete search history.

(56) References Cited

U.S. PATENT DOCUMENTS

| | | |
|---|---|---|
| 2005/0119568 A1 | 6/2005 | Salcudean et al. |
| 2010/0007357 A1 | 1/2010 | Ammari et al. |
| 2014/0323862 A1 | 10/2014 | Silverman et al. |

FOREIGN PATENT DOCUMENTS

| | | |
|---|---|---|
| JP | 2010-125260 | 6/2010 |
| WO | 2014/138997 | 9/2014 |
| WO | 2015/168400 | 11/2015 |

OTHER PUBLICATIONS

Ripken et al., "fs-Laser induced elasticity changes to improve presbyopic lens accommodation", Graefes Arch Clin Exp Ophthalmol, 2008, pp. 897-906, vol. 246, Springer.
(Continued)

*Primary Examiner* — Jack Dinh
(74) *Attorney, Agent, or Firm* — Jackson Walker LLP

(57) ABSTRACT

An excitation force (internal or external) and phase-sensitive optical coherence elastography (OCE) system, used in conjunction with a data analyzing algorithm, is capable of measuring and quantifying biomechanical parameters of tissues in situ and in vivo. The method was approbated and demonstrated on an example of the system that combines a pulsed ultrasound system capable of producing an acoustic radiation force on the crystalline lens surface and a phase-sensitive optical coherence tomography (OCT) system for measuring the lens displacement caused by the acoustic radiation force. The method allows noninvasive and nondestructive quantification of tissue mechanical properties. The noninvasive measurement method also utilizes phase-stabilized swept source optical coherence elastography (PhS-
(Continued)

SSOCE) to distinguish between tissue stiffness, such as that attributable to disease, and effects on measured stiffness that result from external factors, such as pressure applied to the tissue. Preferably, the method is used to detect tissue stiffness and to evaluate the presence of its stiffness even if it is affected by other factors such as intraocular pressure (IOP) in the case of cornea, sclera, or the lens. This noninvasive method can evaluate the biomechanical properties of the tissues in vivo for detecting the onset and progression of degenerative or other diseases (such as keratoconus).

7 Claims, 11 Drawing Sheets

Related U.S. Application Data

(60) Provisional application No. 62/077,561, filed on Nov. 10, 2014, provisional application No. 62/171,043, filed on Jun. 4, 2015.

(51) Int. Cl.
   A61B 8/08 (2006.01)
   A61B 8/10 (2006.01)
   A61B 3/10 (2006.01)
   A61B 5/00 (2006.01)

(52) U.S. Cl.
   CPC .......... *A61B 5/0051* (2013.01); *A61B 5/0053* (2013.01); *A61B 5/0066* (2013.01); *A61B 5/0093* (2013.01); *A61B 8/10* (2013.01); *A61B 8/485* (2013.01); *A61B 5/0097* (2013.01); *A61B 2576/00* (2013.01)

(56) References Cited

OTHER PUBLICATIONS

Mello et al., "Femtosecond laser photodisruption of the crystalline lens for restoring accommodation", International Ophthalmology Clinics, 2011, pp. 87-95, vol. 51, No. 2.
Sinkus et al., "Elasticity Imaging via MRI: Basics, Overcoming the waveguide limit, and clinical liver results", Cirrent Medical Imaging Reviews, 2012, pp. 56-63, vol. 8.
Garra, "Imaging and Estimation of Tissue Elasticity by Ultrasound", Ultrasound Quarterly, Review Article: CME Article, 2007, pp. 255-268, vol. 23, No. 4.
Kennedy et al., "Analysis of mechanical contrast in optical coherence elastography", Journal of Biomedical Optics, 2013, pp. (121508-1)-(121508-12), vol. 18, No. 12.
Qi et al., "Confocal acoustic radiation force optical coherence elastography using a ring ultrasonic transducer", Applied Physics Letters, 2014, pp. (123702-1)-(123702-4), vol. 104.
Razani et al., "Optical coherence tomography detection of shear wave propagation in inhomogeneous tissue equivalent phantoms and ex-vivo carotid artery samples", Biomedical Optics Express, 2014, pp. 895-906, vol. 5, No. 3.
Aglyamov, et al. "Assessment of the depth-dependence of the mechanical parameters of a layered medium using surface excitation and motion measurements on the surface", Ultrasonics Symposium (IUS), 2013 IEEE International, 2013, pp. 1252-1255.
Duck, "Medical and non-medical protection standards for ultrasound and infrasound", Progress in Biophysics and Molecular Biology, 2007, pp. 176-191, vol. 93.
Muthupillai et al., "Magnetic-resonance elastography by direct visualization of propagating acoustic strain waves", Science, 1995, pp. 1854-1857, vol. 269, No. 5232.
Lubatschowski et al., "Femtosecond lentotomy: generating gliding planes inside the crystalline lens to regain accommodation ability", J. Biophotonics, 2010, pp. 265-268, vol. 3, No. 5-6.
International Search Report and Written Opinion dated Feb. 15, 2016 for the corresponding PCT Application No. PCT/US2015/059472.
Han et al., "Air Puff Induced Corneal Vibrations: Theoretical Simulations and Clinical Observations", J Refract Surg., 2014, pp. 208-213, vol. 30, No. 3.
Wollensak et al., "Riboflavin/ultraviolet-a-induced collagen crosslinking for the treatment of keratoconus", American Journal of Ophthalmology, 2003, pp. 620-627, vol. 135, No. 5.
Medeiros et al., "Evaluation of the influence of corneal biomechanical properties on Intraocular pressure measurements using the Ocular Response Analyzer", J. Glaucoma., 2006, pp. 364-370, vol. 15, No. 5.
Hernandez-Andrade et al., "Evaluation of cervical stiffness during pregnancy using semiquantitative ultrasound elastography", Ultrasound. Obstet. Gynecol., 2013, pp. 152-161, vol. 41, No. 2.
Li et al., "Air-pulse OCE for assessment of age-related changes in mouse cornea in vivo", Laser Phys. Lett., 2014, pp. 1-4, vol. 1, No. 6, 065601.
Wang et al., "A focused air-pulse system for optical-coherence-tomography-based measurements of tissue elasticity", Laser Phys. Lett., 2013, pp. 1-6, vol. 10, No. 7, 075605.
Wang et al., "Noncontact measurement of elasticity for the detection of soft-tissue tumors using phase-sensitive optical coherence tomography combined with a focused air-puff system", Opt Lett. 2012, pp. 5184-5186, vol. 37, No. 24.
Tao et al., "Effects of Collagen Cross-Linking on the Interlamellar Cohesive Strength of Porcine Cornea," Cornea, 2013, pp. 169-173, vol. 32, No. 2.
Twa et al., "Spatial characterization of corneal biomechanical properties with optical coherence elastography after UV cross-linking," Biomedical Optics Express, 2014, pp. 1419-1427, vol. 5, No. 5.
Kotecha et al., "Biomechanical parameters of the cornea measured with the Ocular Response Analyzer in normal eyes," BMC Ophthalmology, 2014, pp. 1-7, vol. 14, Issue, 1, No. 11.
Charman, "The eye in focus: accommodation and presbyopia," Clinical and Experimental Optometry, 2008, pp. 207-225, vol. 91, No. 3.
Glasser et al., "Presbyopia and the optical changes in the human crystalline lens with age," Vision Res., 1998, pp. 209-229, vol. 38, No. 2.
Glasser et al., "Aging of the human crystalline lens and presbyopia," Int. Ophthalmol. Clin., 2001, pp. 1-15, vol. 41.
Heys et al., "Massive increase in the stiffness of the human lens nucleus with age: the basis for presbyopia?" Molecular Vision, 2004, pp. 956-963, vol. 10.
Yoon et al., "The mechanical properties of ex vivo bovine and porcine crystalline lenses: age-related changes and location-dependent variations," Ultrasound Med. Biol., 2013, pp. 1120-1127 vol. 39, No. 6.
Reilly et al., "Microindentation of the young porcine ocular lens," Journal of Biomechanical Engineering, 2009, pp. 044502-1-4, vol. 131.
Erpelding et al., "Mapping age-related elasticity changes in porcine lenses using bubble-based acoustic radiation force," Exp Eye Res., 2007, pp. 332-341, vol. 84, No. 2.
Hollman et al., "Mapping elasticity in human lenses using bubble-based acoustic radiation force," Exp Eye Res., 2007, pp. 890-893, vol. 85, No. 6.
Glasser, "Restoration of accommodation: surgical options for correction of presbyopia," Clin Exp Optom, 2008, pp. 279-295, vol. 91, No. 3.
Schumacher et al., "Femtosecond laser induced flexibility change of human donor lenses," Vision Research, 2009, pp. 1853-1859, vol. 49.
Sarvazyan et al., "An overview of elastography-an emerging branch of medical imaging," Curr. Med. Imaging Rev.. 2011, pp. 255-282, vol. 7, No. 4.
Kennedy et al., "In vivo three-dimensional optical coherence elastography," Opt Express, 2011, pp. 6623-6634, vol. 19, No. 7.
Yoon et al., "High pulse repetition frequency ultrasound system for the ex vivo measurement of mechanical properties of crystalline

(56) References Cited

OTHER PUBLICATIONS lenses with laser-induced microbubbles interrogated by acoustic radiation force," Phys Med Biol., 2012, pp. 4871-4884, vol. 57, No. 15.
Scarcelli et al., "In vivo Brillouin optical microscopy of the human eye," Opt Express, 2012, pp. 9197-9202, vol. 20, No. 8.
Scarcelli et al., "In vivo measurement of age-related stiffening in the crystalline lens by Brillouin optical microscopy," Biophys J., 2011, pp. 1539-1545, vol. 101, No. 6.
Bailey et al., "Light-scattering study of the normal human eye lens: elastic properties and age dependence," IEEE T Bio-Med. Eng., 2010, pp. 2910-2917, vol. 57, No. 12.
Reiß et al. "Spatially resolved Brillouin spectroscopy to determine the rheological properties of the eye lens," Biomed Opt Express, 2011, pp. 2144-2159, vol. 2, No. 8.
Qi et al., "Phase-resolved acoustic radiation force optical coherence elastography," J. Biomed Opt., 2012, pp. 1-3, vol. 17, No. 11.
Wang et al., "Phase-sensitive optical coherence elastography for mapping tissue microstrains in real time," Appl Phys Lett., 2007, vol. 90, No. 16, 164105.
Sun et al., "Optical coherence elastography: current status and future applications," J Biomed Opt., 2011, pp. 1-12, vol. 16, No. 4.
Liang et al., "Optical micro-scale mapping of dynamic biomechanical tissue properties," Opt. Express, 2008, pp. 11052-11065, vol. 16, No. 5.
Kennedy et al., "Optical palpation: optical coherence tomography-based tactile imaging using a compliant sensor," Opt Lett., 2014, pp. 3014-3017, vol. 39, No. 10.
Rogowska et al., "Optical coherence tomographic elastography technique for measuring deformation and strain of atherosclerotic tissues," Heart, 2004, pp. 556-562, vol. 90.
Wang et al., "Shear wave imaging optical coherence tomography (SWI-OCT) for ocular tissue biomechanics," Opt Lett., 2014, pp. 41-44, vol. 39, No. 1.
Wang et al. "Detection and monitoring of microparticles under skin by optical coherence tomography as an approach to continuous glucose sensing using implanted retroreflectors," IEEE Sens J., 2013, pp. 4534-4541, vol. 13, No. 11.
Aglyamov et al., "Model-based optical coherence elastography using acoustic radiation force," Proc. SPIE, vol. 8946, Optical Elastography and Tissue Biomechanics, 2014, 89460T.
Aglyamov et al., "Model-based reconstructive elasticity imaging using ultrasound," Int. J. Biomed. Imaging, 2007, pp. 1-11, vol. 2007, ID, 35830.
Ziebarth et al., "Atomic force microscopy measurements of lens elasticity in monkey eyes," Molecular Vision. 2007, pp. 504-510, vol. 13.
Wang et al., "Assessing the mechanical properties of tissue-mimicking phantoms at different depths as an approach to measure biomechanical gradient of crystalline lens," Biomed Opt Express, 2013, pp. 2769-2780, vol. 4, No. 12.
Ruberti et al., "Corneal Biomechanics and Biomaterials", Annual review of biomedical engineering, 2011, pp. 269-295, vol. 13.
Li et al., "Dynamic OCE measurement of the biomechanical properties of gelatin phantom and mouse cornea in vivo", Proc. of SPIE, 2013, pp. (85711T-1)-(85711T-8), vol. 8571, Optical Coherence Tomography and Coherence Domain Optical Methods in Biomedicine XVII.
Liu et al., "Corneal Stiffness Affects IOP Elevation during Rapid Volume Change in the Eye", Investigative ophthalmology & visual science, 2009, pp. 2224-2229, vol. 50, No. 5.
Kennedy et al., "A Review of Optical Coherence Elastography: Fundamentals, Techniques and Prospects", IEEE Journal of Selected Topics in Quantum Electronics, 2014, vol. 20, No. 2.
Venkatesh et al., "Magnetic Resonance Elastography of Liver: Technique, Analysis, and Clinical Applications", Journal of Magnetic Resonance imaging, 2013, pp. 544-555, vol. 37, No. 3.
Liang et al., "Biomechanical Properties of In Vivo Human Skin From Dynamic Optical Coherence Elastography", IEEE Trans Biomed Eng., 2010, pp. 953-959, vol. 57, No. 4.
Li et al., "Quantitative elastography provided by surface acoustic waves measured by phase-sensitive optical coherence tomography", Optics Letters, 2012, pp. 722-724, vol. 37, No. 4.
Doyle, "Wave Propagation in Structures: Spectral Analysis Using Fast Discrete Fourier Transform", 1997, pp. 198-274, 2nd edition, Springer-Verlag, New York (1997).
Singh et al., "Study of gelatin-agar intermolecular aggregates in the supernatant of its coacervate," Colloids and surfaces B: Biointerfaces, 2007, pp. 29-36, vol. 57, No. 1.
Pau, et al., "The increasing sclerosis of the human lens with age and its relevance to accommodation and presbyopia", Graefe's Arch Clin Exp Ophthalmol, 1991, pp. 294-296, vol. 229.

OPTICAL COHERENCE ELASTOGRAPHY TO ASSESS BIOMECHANICS AND DETECT PROGRESSION OF OCULAR AND OTHER TISSUES DEGENERATIVE DISEASES

This application is a continuation application of and claims priority to U.S. patent application Ser. No. 14/934,663, filed Nov. 6, 2015, entitled "Optical Coherence Elastography to Assess Biomechanics and Detect Progression of Ocular and Other Tissues Degenerative Diseases," which claims priority to U.S. Provisional Patent Application Ser. No. 62/077,561, filed Nov. 10, 2014, entitled "Optical Coherence Elastography to Detect the Onset and Progression of Corneal Degenerative Diseases," and U.S. Provisional Patent Application Ser. No. 62/171,043, filed Jun. 4, 2015, entitled "Ultrasound and Optical Coherence Elastography to Assess Biomechanics of Ocular and Other Tissues," and the entire contents of these applications are hereby incorporated by reference.

The present invention used in part funds from the National Institute of Health (NIH), Nos. 1R01EY022362, 1R01EY014225, 1R01HL120140, U54HG006348 and the DOD/NAVSEA, No. PRJ71TN. The United States Government has certain rights in the invention.

BACKGROUND

This disclosure pertains to a method for assessing changes in biomechanical properties of ocular and other tissues and for detecting and differentiating tissue stiffness using optical coherence elastography (OCE).

The changes in viscoelastic properties of the tissues are associated with onset and progression of different diseases. Therefore, it is important to assess and quantify tissue mechanical properties during disease progression and application of different therapeutic procedures.

For example, keratoconus is associated with localized reduced rigidity of the cornea, and the information of the corneal stiffness is useful to provide improved diagnosis and monitoring of this pathological status. Also, real-time in vivo measurement of the spatial elasticity distribution with microscopic scale in the cornea could lead to adaptive mechanical modeling of the individual corneal structure which is extremely important to prevent over-corrections, under-corrections and ectasia from refractive surgeries, such as LASIK, and to further optimize the laser ablation procedures.

Structurally degenerative diseases such as keratoconus can significantly alter the stiffness of the cornea, directly affecting the quality of vision. Keratoconus can pathologically decrease the stiffness of the cornea, leading to a loss in the quality of vision. Detecting changes in the biomechanical properties of ocular tissues, such as stiffness of the cornea, can aid in the diagnosis of these structurally degenerative diseases.

As another example, changes in mechanical properties of crystalline lens play an important role in the development of presbyopia, which is the progressive, age-related loss of accommodation of the eye. Results of ex-vivo studies have shown that the stiffness of crystalline lenses increases with age for animals and humans. The increase in lens stiffness is generally believed to be responsible for the progressive loss of the ability of the lens to change shape, leading to presbyopia. However, current understanding of the mechanical properties of the lens, its changes with age, and its role in presbyopia is limited, in part due to a lack of technology that allows measurements of the mechanical properties of the lens in situ and in vivo. The location of the crystalline lens inside the eye makes it challenging to measure its mechanical properties in vivo or in situ (i.e., inside the globe).

UV-induced collagen cross-linking (CXL) is an emerging treatment that effectively increases corneal stiffness and is applied clinically to treat keratoconus. The effectiveness of this treatment may be analyzed by measuring the corneal stiffness both before and after treatment. However, measured corneal stiffness is also influenced by intraocular pressure (IOP). Therefore, experimentally measured changes in corneal stiffness may be attributable to the effects of CXL, changes in IOP, or both. There is a possibility that a cornea, particularly after treatment with CXL, may still be structurally weakened by keratoconus, yet have a "normal" measured stiffness due to an elevated IOP. Current techniques are not able to measure the true IOP in vivo without consideration of the effect of the biomechanical properties of the cornea. Distinguishing corneas that have the same measured stiffness but are at different IOPs is still a challenge.

Elastography is an emerging technique that can map the local mechanical properties of tissues. Ultrasound elastography (USE) and magnetic resonance elastography (MRE) have experienced rapid development during the past few years as diagnostic tools. One common principle of these techniques is correlating tissue deformation caused by the external mechanical excitation to tissue elasticity. In previous studies, acoustic radiation force was applied to a microbubble created by laser-induced optical breakdown in the lens. The displacement of the microbubble was measured by ultrasound and used to evaluate lens elasticity. However, such approach is required to produce microbubbles within the lens. The basic feasibility of using Brillouin microscopy to measure the lens bulk modulus both in vitro and in vivo has been explored. Brillouin microscopy can be implemented using simple instrumentation, but it has a relatively slow acquisition time. There is also uncertainty on how to correlate Brillouin shift (modulus) to the classical mechanical description of the tissues (e.g. Young modulus). USE and MRE can assess mechanical properties of tissue but the relatively low spatial resolution of USE and MRE is still a critical limitation for certain applications, particularly for ocular tissues and also for measurements at the cellular level.

What is needed, therefore, is an improved, non-invasive and highly sensitive method to assess the mechanical properties of the ocular and other tissues with high resolution and sensitivity.

SUMMARY

The present disclosure relates generally to methods and systems for assessing the biomechanical properties of tissues non-invasively, to a method using optical coherence elastography (OCE) for detecting tissue stiffness, such as corneal or lens stiffness, and for differentiating samples having similar measured stiffness as a result of other influences, such as intraocular pressure (IOP). The methods described herein for tissue biomechanical quantification are demonstrated in the case of the cornea and crystalline lens but generally applicable for all soft and hard tissues in the body.

Optical coherence elastography (OCE) is capable of direct and high resolution assessment of mechanical properties of tissue and, therefore, overcomes the limitations of previously-used techniques. OCE employs high-resolution optical coherence tomography (OCT) to detect the sample deformation induced by an external force. In comparison to ultrasound elastography (USE) and magnetic resonance elastography (MRE), OCE is able to provide superior spatial imaging resolution, faster acquisition speed, and greater displacement sensitivity.

In one aspect, this disclosure relates to a method for quantifying biomechanical properties of a tissue, comprising: producing an external or internal force to stimulate localized deformation on a surface of the tissue; using an optical coherence tomography (OCT) or any other low-coherence interferometry subsystem to measure an induced displacement profile resulting from the localized deformation on the surface of the tissue; and quantifying the biomechanical properties of the tissue based on the analysis of the induced elastic wave (i.e. temporal or spatial displacement profile analysis) using an algorithm.

The present system combines a pulsed ultrasound system (or any other excitation methods such as air-puff, laser pulse, etc) capable of producing a force on the tissue surface and a phase-sensitive OCT system for measuring the tissue displacement caused by the force. The system allows for a non-invasive and highly sensitive method to assess the mechanical properties of the tissue in vivo.

The present noninvasive measurement method also uses phase-stabilized swept source optical coherence elastography (PhS-SSOCE) to distinguish between corneal stiffness attributable to disease or UV-induced collagen cross-linking (CXL) and IOP effects on measured corneal stiffness. Optical coherence elastography (OCE) is an emerging noninvasive technique used in recent years that can map the local biomechanical properties of tissue. Similar to ultrasound elastography (USE) and magnetic resonance elastography (MRE), OCE is usually comprised of an external loading component that produces displacements within the tissue. In OCE, imaging this tissue displacement is performed with optical coherence tomography (OCT), which has superior spatial resolution compared to USE and MRE. From the velocity of an induced elastic wave (EW), or stress-strain curve measured by OCE, tissue elasticity can be quantitatively estimated.

The present method compares the displacement amplitude attenuation, elastic wave speed, dispersion of the elastic waves, and natural frequency of the vibrations of a focused air-pulse induced elastic wave in corneal tissue. The damping speed of the displacement amplitudes at each measurement position along the wave propagation are compared for the different materials. This noninvasive method has the potential to detect the early stages of ocular diseases such as keratoconus or to be applied during CLX procedures by factoring in the effects of IOP on measured corneal stiffness.

FIG. 1 shows a flow chart illustrating an example of a method encompassed by the present disclosure. Generally, in the first step of the method, an elastic wave is generated in two corneal tissue samples, preferably by a focused air pulse. The elastic wave is detected using PhS-SSOCE at different positions along the wave propagation. If the measured elasticity is different, then the two samples can be differentiated without additional measurement. If the measured elasticity is the same, or at least so close that additional measurement is warranted, then additional steps are taken. The wave displacement is normalized by dividing the amplitude at each measured position by the amplitude at the excitation position. Then, the attenuation of the normalized elastic wave displacement is compared. The sample that has the faster attenuation has a higher viscosity than the other sample, allowing for the samples to be differentiated.

DETAILED DESCRIPTION OF PREFERRED EMBODIMENTS

Figure 1:
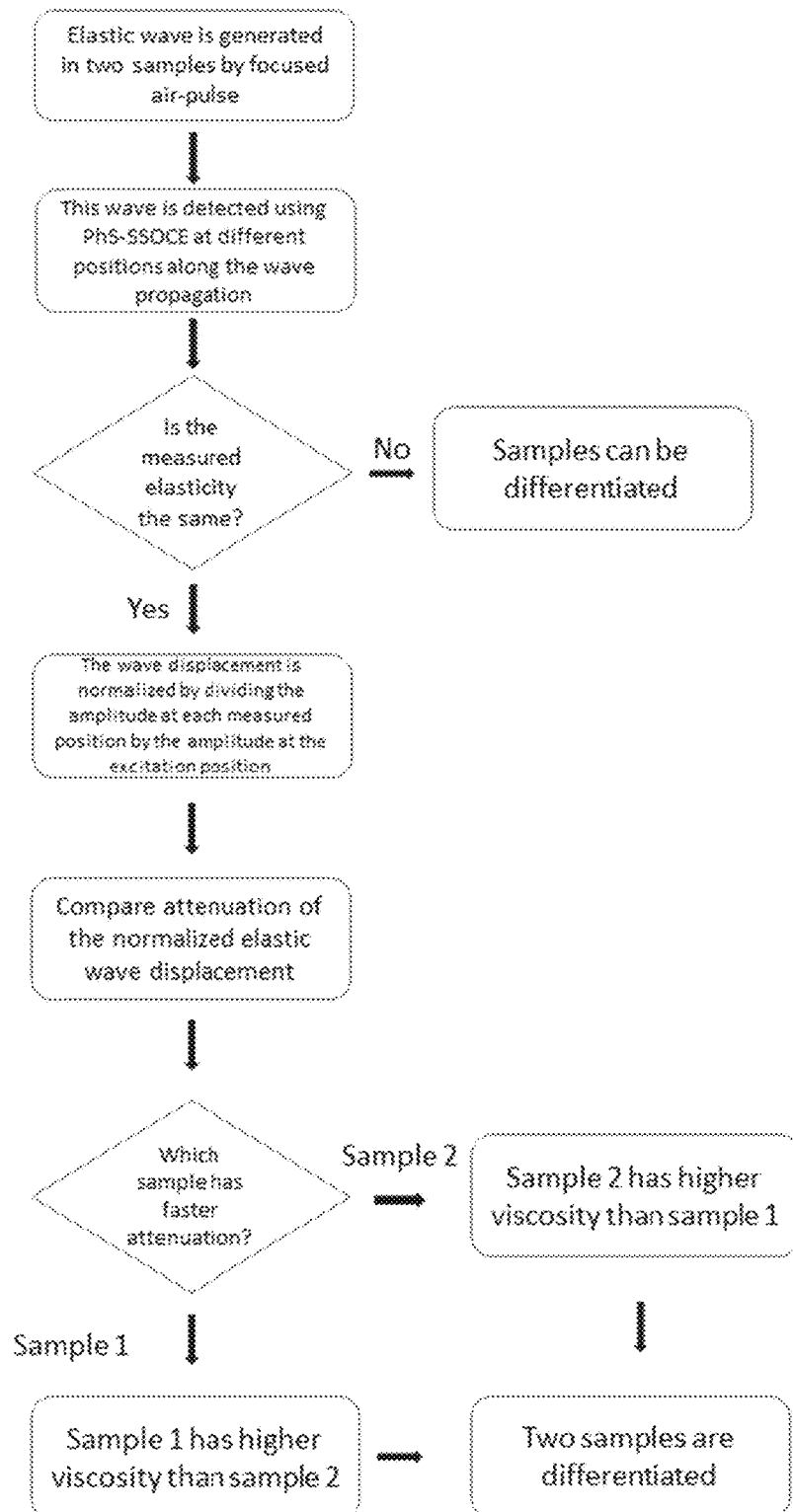
FIG. 1 shows a flow chart describing an exemplary method for differentiating samples based on elastic wave measurements and phase-stabilized swept source optical coherence elastography (PhS-SSOCE).

The present disclosure relates to methods utilizing optical coherence elastography (OCE) to detect tissue stiffness and to distinguish the effects of other factors that might affect tissue stiffness. Previous studies have demonstrated that OCE is feasible for quantitatively assessing the elasticity of a sample. Preferably, the method is used to detect corneal stiffness and to evaluate the presence of corneal stiffness even if it is affected by intraocular pressure (IOP). The present method uses phase-stabilized swept source optical coherence elastography (PhS-SSOCE) and can distinguish untreated (UT) and UV-induced collagen cross-linked (CXL) corneas of the same measured stiffness but at different IOPs. This noninvasive method can evaluate the biomechanical properties of the cornea in vivo for detecting the onset and progression of corneal degenerative diseases such as keratoconus.

Generally, the present method is for measuring tissue biomechanical properties (e.g. stiffness) and for differentiating tissue samples using optical coherence elastography. In an exemplary embodiment, a first step is inducing elastic waves in the tissue samples, followed by detecting properties of the waves using interferometry (low-coherence interferometry or optical coherence tomography is preferred) at different measurement positions along the waves (or at the same position for temporal analysis of the elastic wave displacement profile), wherein the detected properties include measured wave velocities and measured wave displacement amplitudes. A next step is determining elasticities of the tissue samples using the measured wave velocities and then differentiating the tissue samples having different measured wave velocities. For those samples having similar measured wave velocities and needing further differentiation, a next step is normalizing the measured wave displacement amplitudes to produce normalized wave displacement data. The normalized wave displacement data is then used to identify tissue samples having faster wave attenuation and slower wave attenuation. The tissue samples having faster wave attenuation are then classified as tissue sample having increased viscosity and reduced stiffness and the tissue samples having slower wave attenuation are classified as tissue samples having reduced viscosity and increased stiffness.

In preferred embodiments, the tissue samples are ocular tissue samples. In addition, the step of inducing elastic waves may be by directing a focused air-pulse on the tissue samples. The step of determining elasticities of the tissue samples is preferably by calculating Young's modulus using the measured wave velocities. The step of normalizing the measured wave displacement amplitudes is preferably by dividing the measured wave displacement amplitudes at the different measurement positions along the waves by the measured wave displacement amplitude at an excitation position. The step of using the normalized wave displacement data to identify tissue samples having faster wave attenuation and slower wave attenuation preferably involves calculating a customized ratio between normalized data collected at various positions for two samples, as described more fully below. This step can be repeated for additional pairs of samples.

The present disclosure also relates to a co-aligned focused ultrasound (or any other excitation methods such as air-puff, laser pulse, etc.) and phase-sensitive optical coherence elastography (US-OCE) system for assessment of biomechanical properties of tissues, including in situ and in vivo.

An example demonstrated herein is the use of ultrasound radiation as the excitation force and crystalline lens as the target. However, any type of the excitation force (external or internal) or any ocular or other tissues could be used with this method.

Figure 2:
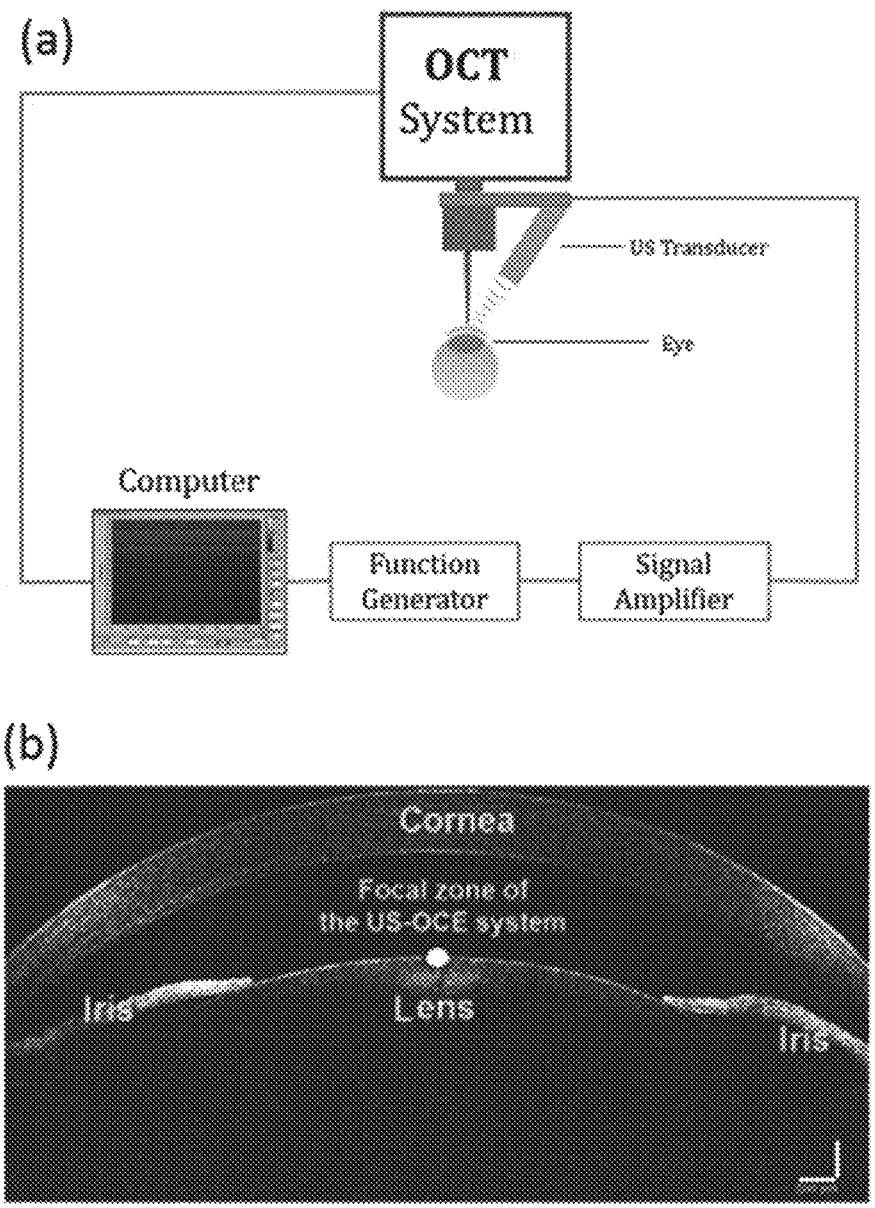
FIG. 2 shows an example of (a) a schematic of the co-aligned ultrasound and optical coherence elastography (US-OCE) system and (b) a typical optical coherence tomography (OCT) image of a crystalline lens.

The exemplary US-OCE system includes an ultrasound delivery sub-system that emits acoustic force to stimulate localized deformation on the crystalline lens surface and an optical coherence tomography (OCT) sub-system to measure the induced displacement profile. The US-OCE system is preferably used in conjunction with a data analyzing algorithm. Based on measurements from the US-OCE system, the data analyzing algorithm can quantify the mechanical parameters of the crystalline lens. Any suitable computer or data processor programmed with the data analyzing algorithm can be used to make these calculations. The mechanical parameters include parameters such as displacement amplitude, natural frequency, Young's modulus, and shear viscosity of the crystalline lens. The kinematical differential equation can be used to describe the lens's relaxation process starting from the maximum displacement point:

$$\frac{d^2 y(t)}{dt^2} + 2\xi\omega\frac{dy(t)}{dt} + \omega^2 y(t) = 0, \quad (1)$$

where $\xi=c/(2\sqrt{mk})$ is the damping ratio and $\omega=\sqrt{k/m}$ is the undamped natural frequency of the dynamic system. The analytical solution of equation (1) is $$y(t)=A(1+bt)e^{-\omega t} \quad (2)$$

when $\xi=1$; equation (2) can be used to calculate natural frequency. An analytical solution of the spectral component of the vertical displacement in the frequency domain can be derive:

$$Y_z(r,z) = -\int_0^\infty \alpha^2 J_0(\alpha r)[A_1 e^{-\alpha z} - A_2 e^{\alpha z} + \alpha(B_1 e^{-\beta z} + B_2 e^{\beta z})]d\alpha, \quad (3)$$

where $J_0$ and $J_1$ are Bessel functions of order 0 and 1, respectively. Using the analytical solution of the forward problem (3), reconstruction of Young's modulus and shear viscosity was posed as a minimization problem FIG. 2(a) shows a schematic of an example of the co-aligned US-OCE system. The setup consists of the Ultrasound (US) excitation system and OCT detection system. The function generator and the amplifier are used to drive the ultrasound transducer. FIG. 2(b) shows an example of a typical OCT image of a lens.

For experimental validation, the biomechanical properties of rabbit crystalline lenses were assessed in situ by using a US-OCE system. Experiments were performed on the lenses of young and mature rabbits in situ (lens located inside an eye globe). Both the maximum displacement and the relaxation rate of the displacement were analyzed. Also, a model-based reconstruction was applied to quantify the viscoelastic properties of the lenses. For validation, uniaxial mechanical compression tests (considered as a "gold standard") were conducted on the same young and mature rabbit lenses. The US-OCE system, which combines acoustic radiation force excitation and phase-sensitive OCT, was demonstrated as a promising tool for noninvasive assessment of the changes in the biomechanical properties of the crystalline lens in situ. The high displacement sensitivity of phase-resolved OCT detection enables the measurement of sub-micron displacements on the lens surface, which is critical for in vivo study as it allows for the application of a minimal acoustic radiation force to induce a detectable displacement and minimizes the potential ultrasound damage to the eye. In addition, the high spatial resolution of OCT allows highly-localized investigation of the mechanical properties of the lens.

Example 1. Measurement and Validation

A PhS-SSOCE system was utilized which consisted of a focused air-pulse delivery system and a phase-stabilized swept-source OCT (PhS-SSOCT) system. A short duration focused air-pulse was expelled through an electronic solenoid controlled air gate and induced an elastic wave in the sample. A pressure gauge provided air source pressure control and measurement. The localized air-pulse excitation was positioned with a 3-D linear micrometer stage. The PhS-SSOCT system was comprised of a broadband swept laser source (HSL2000, Santec, Inc., Torrance, Calif.) with central wavelength of 1310 nm, bandwidth of ~150 nm, scan rate of 30 kHz, and output power of ~29 mW. A-scan acquisition was triggered by a fiber Bragg grating. The axial resolution of the system was ~11 μm in air. The experimentally measured phase stability of the system was ~16 mrad, which corresponded to ~3.3 nm displacement in air. By synchronizing the focused air-pulse with consecutive M-mode images, the elastic wave velocity and a two dimensional depth resolved elasticity were calculated.

Figure 3:
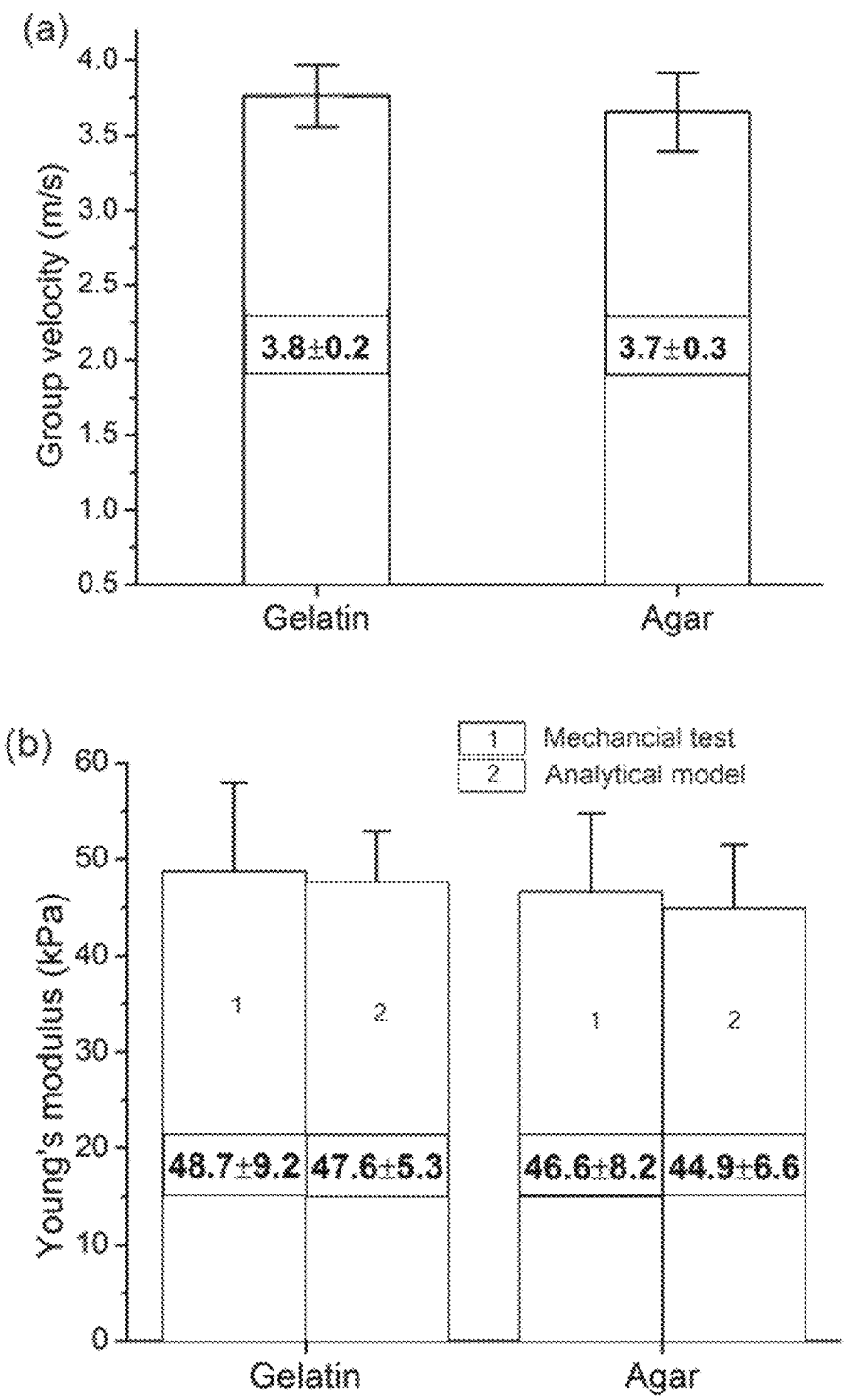
FIG. 3 shows (a) elastic wave (EW) velocities of 14.0% gelatin (w/w) and 1.1% (w/w) agar phantom samples measured by PhS-SSOCE; and (b) a comparison of estimated and measured Young's moduli of the 14.0% gelatin and 1.1% agar phantoms.

A validation study was initially conducted on 14.0% gelatin (w/w) and 1.1% agar (w/w) phantom samples (n=5 for each type) with the same cylindrical dimensions of diameter D=33 mm and height H=11 mm. As shown in FIG. 3(a), the EW velocity, c, measured by PhS-SSOCE in the gelatin samples was 3.76±0.2 m/s, which was very similar to the EW velocity in the agar samples of 3.64±0.3 m/s. The acoustic surface wave formula (equation 1, below) was used to estimate the Young's moduli of the samples, where the density, $\rho=1.02$ kg/m$^3$ and Possion ratio, $\upsilon=0.49$.

$$E = \frac{2\rho(1+\upsilon)^3 c^2}{(0.87+1.12\upsilon)^2} \quad (1)$$

As shown in FIG. 3(b), the Young's modulus for the 14.0% gelatin and 1.1% agar phantoms obtained by the analytical model was 48.7±9.2 kPa and 46.6±8.2 kPa, respectively. Uniaxial mechanical compression tests (Model 5943, Instron Corp., MA) were conducted on the phantoms for elasticity validation. The measured Young's modulus was 47.6±5.3 kPa for the 14% gelatin and 44.9±6.6 kPa for the 1.1% agar phantoms as shown in FIG. 3(b). These results demonstrated that the 14.0% gelatin sample and 1.1% agar phantoms were of similar stiffness confirmed by both analytical model and uniaxial compression tests.

To compare the damping characteristics between any two normalized displacement amplitude attenuation curves of the elastic waves, a customized ratio, r, was used, where ND1i and ND2i were the normalized displacement of the induced elastic wave at the $i^{th}$ measurement position for samples 1 and 2, respectively.

$$r_{(ND_1/ND_2)} = \text{mean}(r_i) \pm std(r_i) \text{ with } r_i = \frac{ND_{1i}}{ND_{2i}}, \quad (2)$$

Displacement amplitudes were normalized by dividing the elastic wave displacement amplitude at each measurement position by the displacement amplitude at the excitation position. If r was significantly greater than 1, the displacement in sample 2 damped faster than in sample 1. If r was significantly less than 1, sample 1 damped faster than sample 2. If r was close to 1, the damping was similar in both samples.

Figure 4:
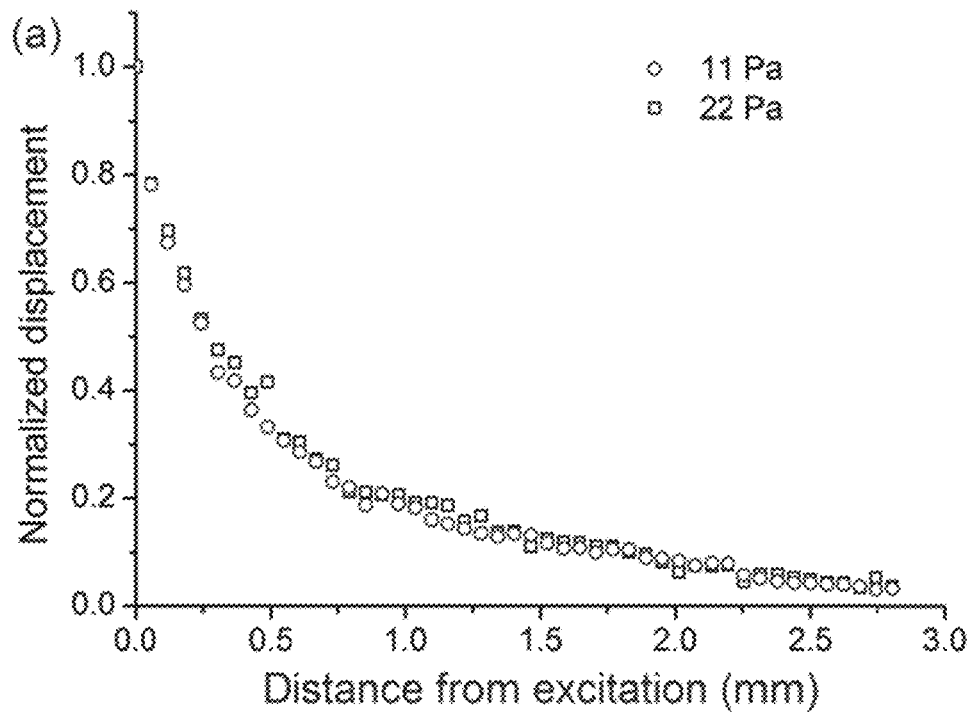
FIG. 4 shows (a) a comparison between the normalized elastic wave displacement amplitude attenuation curves of the 14.0% agar phantom at two different excitation pressures; and (b) a comparison of the normalized elastic wave displacement amplitude attenuation curves of the 14.0% gelatin and 1.1% agar phantoms.
Figure 4:
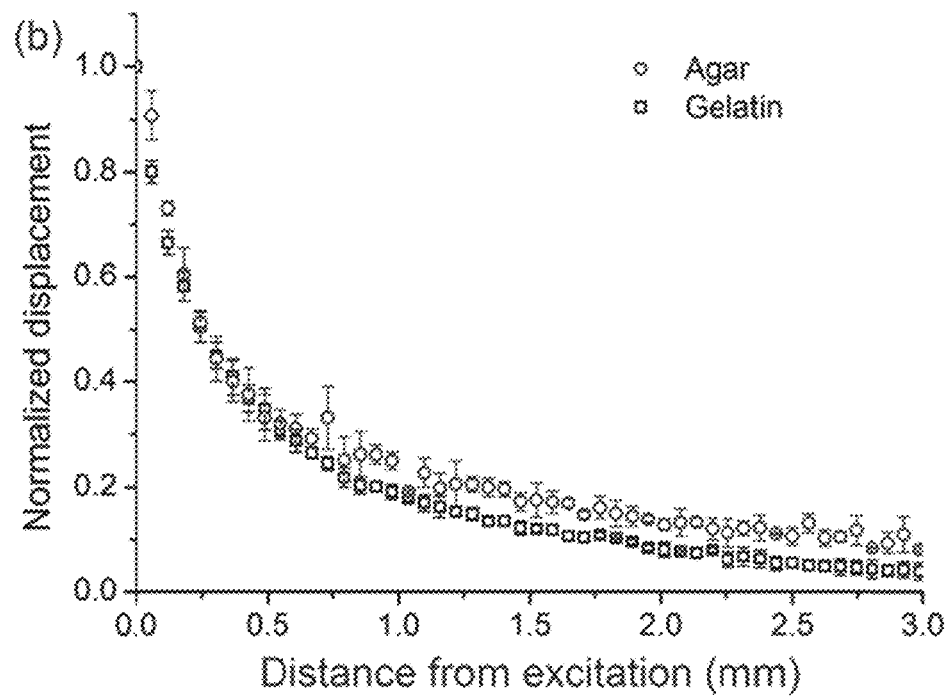

This ratio was first calculated for the same 14.0% gelatin phantom to examine the effects of different initial position displacements by changing the focused air-pulse pressure on the sample to 11 and 22 Pa. The normalized displacement attenuation curves are shown in FIG. 4(a) with the ratio $r_{(22/11)}=0.95\pm0.12$, which was very close to 1. As anticipated, this indicated that the initial displacement amplitude did not affect the damping speed of the elastic wave.

This ratio was then calculated to compare the gelatin and agar phantoms. As shown in FIG. 4(b), the normalized displacement in the agar phantoms was higher than in the gelatin phantoms at the same scan position. By using formula (2), $r_{(agar/gelatin)}=1.56\pm0.47$, which demonstrated that the 14% gelatin damped faster than the 1.1% agar. This result was in agreement with previous findings that gelatin has higher viscosity than agar, which corresponds to faster damping. Therefore, these comparisons showed that this method could be successfully utilized to distinguish two materials of similar stiffness.

Example 2. Corneal Stiffness

To induce a similar measured corneal stiffness in untreated (UT) and UV-induced collagen cross-linked (CXL) porcine corneas, the IOP of the whole eye was controlled by a custom-built controller comprising of a pressure transducer and micro-infusion pump connected in a feedback loop. The elastic wave was measured in a porcine cornea by the PhS-SSOCE system before and after UVA-Riboflavin induced CXL. Elastic wave (EW) measurements were taken at IOPs from 15-35 mmHg with 5 mmHg increments. The EW velocities of the elastic wave in the UT and CXL corneas at the various IOPs are presented in Table 1 below. It can be observed that before CXL, the EW velocity of the cornea at IOP=30 mmHg was calculated as c=3.6±0.4 m/s. After CXL, the EW velocity was 3.6±0.1 m/s at IOP=20 mmHg. Therefore, based on the EW velocity, it might appear that the stiffness of the cornea is the same in those two occurrences.

TABLE 1

| IOP (mmHg) | UT EW velocity (m/s) | CXL EW velocity (m/s) |
|---|---|---|
| 15 | 1.5 ± 0.1 | 2.7 ± 0.1 |
| 20 | 2.3 ± 0.1 | 3.6 ± 0.1 |
| 25 | 3.0 ± 0.3 | 4.0 ± 0.1 |
| 30 | 3.6 ± 0.4 | 4.2 ± 0.2 |
| 35 | 3.7 ± 0.4 | 4.7 ± 0.5 |

Figure 5:
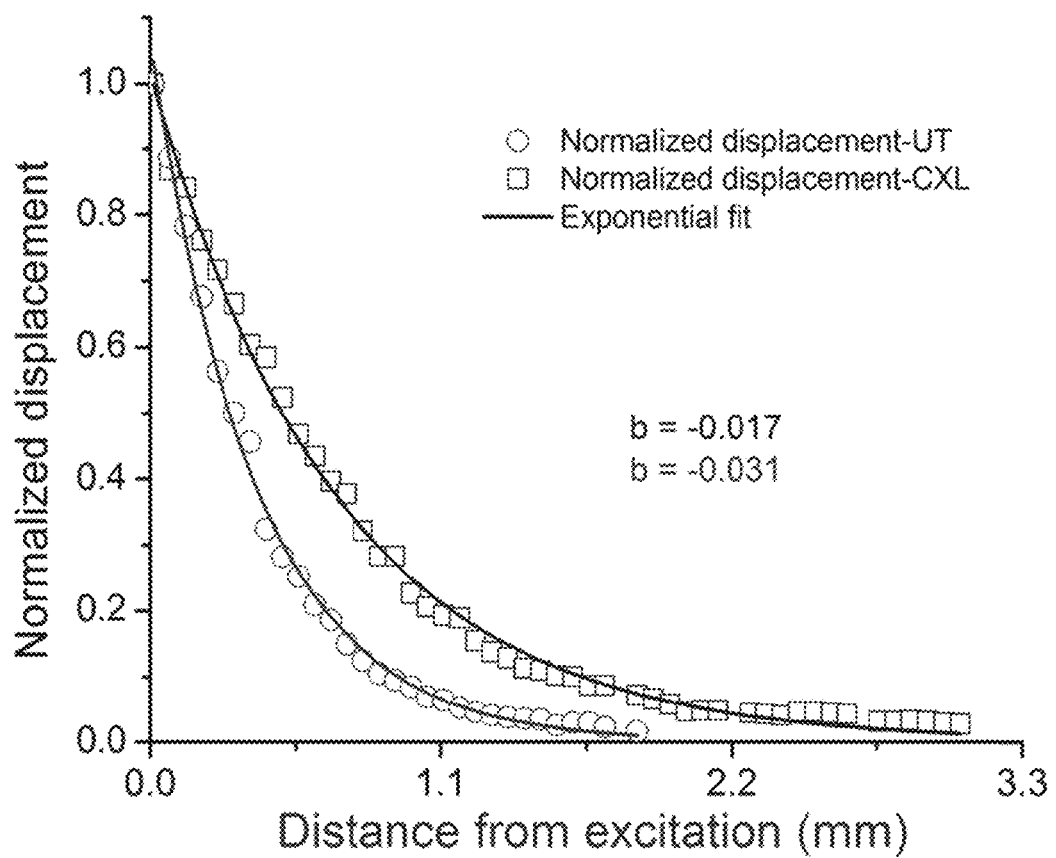
FIG. 5 shows a comparison of the normalized elastic wave displacement amplitude attenuation curves and exponential fit of an untreated (UT) and UV-induced collagen cross-linked (CXL) porcine cornea at the same measured stiffness but different intraocular pressures (IOPs).

After normalizing the elastic wave displacement amplitudes, the damping features of the elastic wave over the measurement positions were analyzed (FIG. 5). Based on formula (2), the ratio of $r_{(CXL/UT)}$ was calculated as r=2.61±0.95, indicating that the damping speed of the cornea had significantly decreased after the CXL treatment. In addition, the normalized displacement attenuation curves were fitted by $y=ae^{bx}$ in which the parameter b was treated as the damping speed. According to the fitted results, the damping speed of the UT cornea ($b_{UT}=-0.031$ mm$^{-1}$) was almost twice the damping speed of the CXL cornea ($b_{CXL}=-0.017$ mm$^{-1}$), which confirmed that the damping speed decreased after CXL treatment. One possible reason for this result is that the CXL treatment is a procedure which displaces water from the cornea tissue. The UT cornea contains more water, which is responsible for a higher viscosity. Therefore, the elastic wave damps faster in the UT cornea than the CXL cornea.

Previous studies have shown that viscosity is negatively correlated with measured corneal stiffness, indicating that the CXL cornea has lower viscosity than the normal one, which corroborates with these results.

Example 3. Experimental System and Sample Preparation

An example of a co-focused and co-localized ultrasound and optical coherence elastography system, termed US-OCE, was developed by combining ultrasound excitation with spectral-domain OCT, as schematically shown in FIG. 2(a). A single element ultrasound transducer (model ISO305HP, CTS Valpey Corporation, MA) with a diameter of about 12.7 mm and a focal length of about 19 mm operating at 3.7 MHz center frequency was employed in the system. A sinusoidal wave with a frequency of 3.7 MHz generated by a 50 MHz function generator (model 80, Wavetek Ltd., CA) was gated by a pulse with duration of 1.1 ms to produce a one-time burst. The driving signal for the ultrasound transducer was amplified using a 40 dB power amplifier (model 350L, Electronics & Innovation Ltd., NY). The acoustic radiation force from the ultrasound wave was used to remotely perturb the anterior surface of the crystalline lens through the cornea and the aqueous humor of the eye.

In the phase-sensitive OCT system, a superluminescent laser diode (model S480-B-I-20, Superlum Diodes Ltd., Ireland) was utilized as the light source with a central wavelength of about 840 nm and a bandwidth of about 49 nm. The laser beam was separated and directed to the reference and the sample arms of a Michelson interferometer. The interference of the combined light from these two arms was detected using a high-resolution spectrometer comprised of a grating and a line-scanning CCD camera (model L104-2k, Basler, Inc., Germany). The A-line acquisition rate of this system was set to 25 kHz during the experiments. A full width at half maximum (FWHM) of the transverse Gaussian profile of the OCT beam at the imaging focal plane was about 8 μm. The system's phase stability measured by the interference signal from the reflection of the two surfaces of a glass slide in the sample arm was ~4 milliradians. However, any OCT or other low-coherence interferometry system, which can measure nanometer to micrometer amplitude displacements, can be used with this method.

A custom-built transducer holder was used to securely attach the ultrasound transducer to the OCT objective lens. The co-alignment of the focal zone of the ultrasound beam and the OCT imaging beam was achieved by aligning the mounted ultrasound transducer with a needle tip. Acoustic radiation force excitation and OCT M-mode imaging (rapidly repeated A-scans at the same location) were synchronized by a computer-generated triggering signal.

Eyes from three young (2-3 months old) and four mature (over 6 months old) rabbits (Pel-Freez Biologicals, LLC, AR) were used in this study. Immediately after enucleating, the globes were placed in a 1× phosphate-buffered solution (PBS, Sigma-Aldrich Inc., MO) and shipped overnight over a dry ice (without freezing). All experiments were performed immediately after receiving the eyes. During the experiments, the entire eye globes were kept in the saline at room temperature to minimize any change in the tissue properties. The sample was positioned in a custom-designed eye holder to prevent motion during the experiment.

The surface of the crystalline lens was placed at the co-aligned focal zone of the US-OCE system. The axis of the OCT beam and, therefore, the direction of the measured displacements was orthogonal to the lens surface. However, the ultrasound transducer was placed at an angle of about 45° relative to the OCT sample beam, so both axial (i.e., vertical or along the axis of the OCT beam) and transverse components of acoustic radiation force were generated. Excitation with the acoustic radiation force produced a perturbation on the lens surface, resulting in a displacement of the lens surface. The displacement of the apex of the crystalline lens as shown in FIG. 2(b) was measured by the phase-sensitive OCT system. Only the axial displacement at the apical position of the lens surface was measured by the US-OCE system. In general, the measured axial displacements are related to the stiffness gradient inside the lens, including the cortex, nucleus, and the lens capsule. The measurements only reflect the elastic properties in the area of the ultrasound excitation where higher elasticity leads to smaller maximum displacement. Since the ultrasound pulses were delivered through a part of the cornea, outside of the optical path of the OCT beam, displacement of the cornea in the OCT image was minimal and did not contribute significantly to the measured signal from the lens surface.

During the experiment, the distance between the sample and the ultrasound transducer was held constant. Therefore, the acoustic radiation force applied on the lens surface can be considered as approximately the same for all the samples, which eliminates the influence from the magnitude of the acoustic radiation force on the amplitude of the displacement on the lens surface.

Example 4. Modeling

Kinematic Model of the Relaxation Process

Under an external acoustic radiation force, the movement of the tissue in the focal zone of US-OCE, shown as a dot in FIG. 2(b), can be separated into forced motion in the response to the acoustic radiation push, and relaxation motion that occurs after the acoustic radiation force is removed and when the external forces are zero.

The following simplified kinematical differential equation can be used to describe the lens's relaxation process starting from the maximum displacement point:

$$m\frac{d^2y(t)}{dt^2} + c\frac{dy(t)}{dt} + ky(t) = 0,$$

where m is the equivalent mass, c is the viscosity coefficient and k is the equivalent spring stiffness. To understand the basic characteristics of the equation, two parameters, $\xi$ and $\omega$, are introduced where $\xi = c/(2\sqrt{mk})$ is the damping ratio and $\omega = \sqrt{k/m}$ is the natural frequency of the dynamic system. The equation then becomes $$\frac{d^2y(t)}{dt^2} + 2\xi\omega\frac{dy(t)}{dt} + \omega^2 y(t) = 0.$$

The analytical solution of the second equation is related to the value of $\xi$ as:

$$y(t) = A(1+bt)e^{-\omega t} \text{ when } \xi=1; \text{ and} \quad (a)$$

$$y(t) = e^{-\xi\omega t}(A\cos\omega_D t + B\sin\omega_D t) \text{ with } \omega_D = \omega\sqrt{1-\xi^2}$$
$$\text{when } 0<\xi<1. \quad (b)$$

Here A, b, and B are the parameters to be determined. According to the exponent forms of the solution of the second equation, ω can also be described as the relaxation rate, which corresponds to the rate of the exponential-type displacement recovery process.

Model for a Viscoelastic Layer

To quantitatively evaluate age-related changes in the viscoelastic properties of the rabbit lenses, a model-based reconstructive approach based on the deformation of a homogeneous viscoelastic layer in response to an acoustic radiation force of short duration was considered. In this approach, tissue is modeled as an incompressible viscoelastic (Voigt body) layer. An acoustic impulse is considered as an axisymmetric force applied to the upper surface of the medium in the direction of the z-axis of the cylindrical system of coordinates (r,θ,z). The mechanical parameters Young's modulus (F), shear viscosity modulus (η), and density (ρ) are constant in the layer. An analytical solution of the spectral component of the axial displacement in the frequency domain can be derived:

$$Y_z(r,z) = -\int_0^\infty \alpha^2 J_0(\alpha r)[A_1 e^{-\alpha z} - A_2 e^{\alpha z} + \alpha(B_1 e^{-\vartheta z} + B_2 e^{\vartheta z})]d\alpha,$$

$$\vartheta = \sqrt{\alpha^2 - k^2}, k^2 = \rho\bar{\omega}^2/(E/3 + i\bar{\omega}\eta),$$

where $J_0$ and $J_1$ are Bessel functions of the order 0 and 1, respectively, and $\bar{\omega}$ is the angular frequency. Four unknown constants $A_1, A_2, B_1$, and $B_2$ are defined using four boundary conditions at the layer boundaries. Fixed boundary conditions for displacement on the bottom of the layer; no shear force on the top surface, and a normal force at the focal point of the transducer are considered. The solution in the time domain was calculated using the inverse Fourier transform after taking into account the duration of the acoustic pulse.

Using the analytical solution of the forward problem, reconstruction of Young's modulus and shear viscosity was posed as a minimization problem, i.e. by minimizing the error function defined as the difference between the measured $y^{exp}$ and theoretically calculated displacements $y^{theory}$ at the point (r=0, z=0):

$$\delta = \|y^{exp} - y^{theory}(E,\eta)\|$$

The density of the lens was assumed to be 1100 kg/m$^3$. To minimize the equation above, a gradient-based iterative procedure was implemented. In the minimization procedure, normalized displacement profiles were used so that only the temporal characteristics of the displacement were taken into account, not the amplitude of the displacements. This approach avoided the influence of the ultrasound beam attenuation and differences in acoustic impedance of the materials such as lens and aqueous humor.

Example 5. Uniaxial Mechanical Compression Tests

After the measurements by the US-OCE system, the eye globes were carefully dissected to extract crystalline lenses for testing with a uniaxial mechanical compression testing system (Model 5943, Instron Corp., MA). The lens was centrally positioned between the compression plates of the device. Prior to the mechanical testing on each lens, a 0.004N pre-loading force was applied. The compression speed was set to 2 mm/minute. The testing was stopped when the vertical displacement reached 30% the whole thickness. Due to the irregular shape of the lens, it was difficult to directly measure the elasticity based on the conventional compression test method. Thus, an equal-volume transformation method was adopted to calculate the stress-strain relationship.

Figure 6:
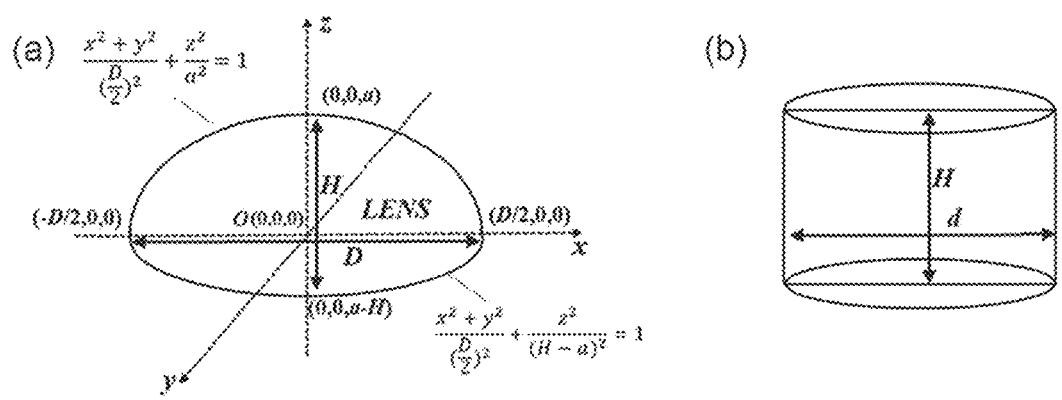
FIG. 6 shows (a) a schematic and mathematical description of a rabbit lens shape and (b) a transformed cylinder with the same volume as the rabbit lens.

As shown in FIG. 6(a), two parameters of a rabbit lens, the height H, and the maximum diameter D, were recorded before the compression test. The volume of the lens was divided into two regions: the upper region, which is above the x-o-y plane, and the lower region which is below the plane. Each part can be simplified as a half ellipsoid, so the upper region can be described by the following formula $(x^2+y^2)/(D/2)^2+z^2/a^2=1$, while the lower part is described as $(x^2+y^2)/(D/2)^2+z^2/(H-a)^2=1$. The whole volume of the lens can then be estimated by the integration:

$$V = V_1 + V_2 = \int_0^a \pi\left(\frac{D}{2}\right)^2\left(1 - \frac{z^2}{a^2}\right)dz + \int_0^{H-a} \pi\left(\frac{D}{2}\right)^2\left(1 - \frac{z^2}{(H-a)^2}\right)dz = \frac{1}{6}\pi HD^2.$$

To estimate the stress-strain relationship of the lens, a cylinder with height H and diameter d, which has the same volume as the lens, was required (FIG. 6(b)). Using the equal-volume equation V=πHd$^2$/4, the cylinder diameter d can be calculated as d=√6/3D Using this equation, the stress can be calculated as σ=4F/(πd$^2$)=6F/(πD$^2$) and ε=L/H, respectively. The stress-strain curve was then fitted by the empirical exponent formula:

$$\sigma = M(e^{N\varepsilon} - 1)$$

where M and N are the parameters to be determined. For each deformation curve, M and N were obtained by using the curve fitting toolbox in MATLAB (Version 2010a, MathWorks Inc., MA). The Young's modulus can be calculated by taking the derivative E=dσ/dε=MNe$^{N\varepsilon}$.

Example 6. Results for Lens

Figure 7:
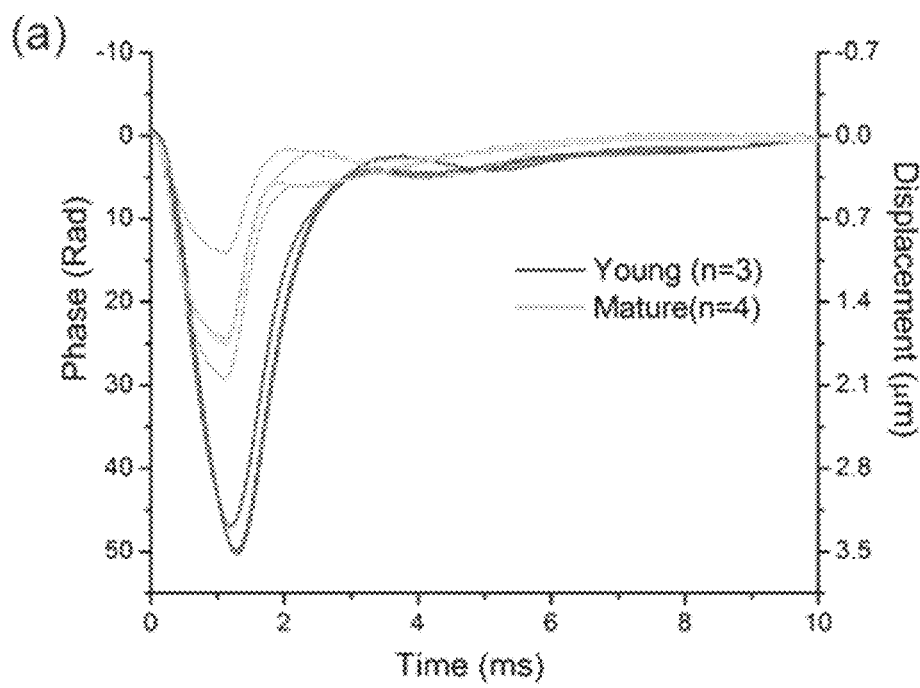
FIG. 7 shows (a) temporal displacement profiles of young (n=3) and mature (n=4) lenses and (b) maximum displacements of the young (n=3) and mature (n=4) lenses.
Figure 7:
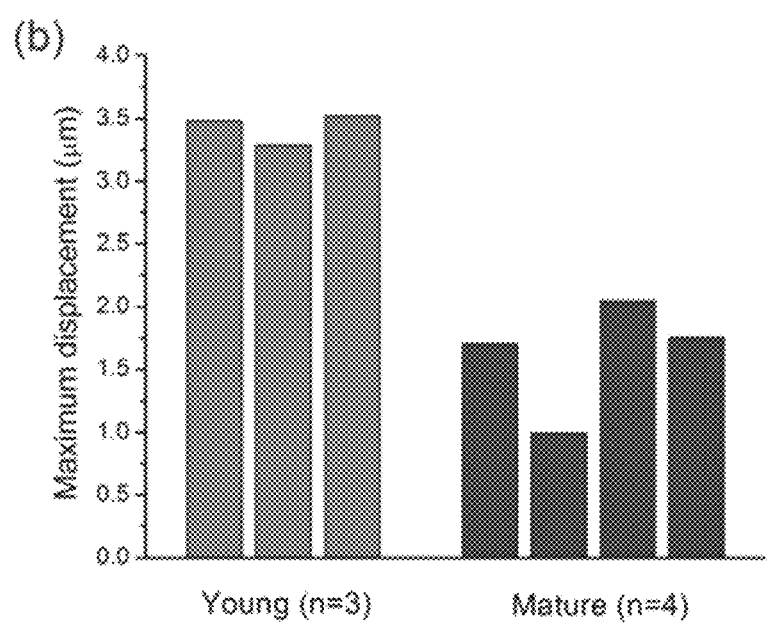

The first parameter used to assess the age-related changes in biomechanical properties of the rabbit lens was the amplitude of the displacements as measured by US-OCE. FIG. 7(a) shows the temporal displacement profiles of typical young and mature lenses. It is clear from either profile that the surface of the crystalline lens starts to deform upon application of the acoustic radiation force. After the removal of the acoustic radiation force, the surface of the lens begins to recover to its original position. Based on the high displacement sensitivity of US-OCE, a minimal acoustic radiation force is sufficient to obtain measurable displacements. Here, the displacement is on the scale of micrometers, which helps ensure that the structural and functional properties of the crystalline lens are not affected. The data presented in FIG. 7(b) clearly demonstrate a significant difference between the maximum displacements of the young and the mature lenses of 3.3±0.1 µm and 1.6±0.4 µm, respectively. It is clear that under the same experimental conditions, the maximum displacement of the young lenses is greater than that of the mature lenses, which is an indicator that the mature lenses are stiffer than the young lenses.

Figure 8:
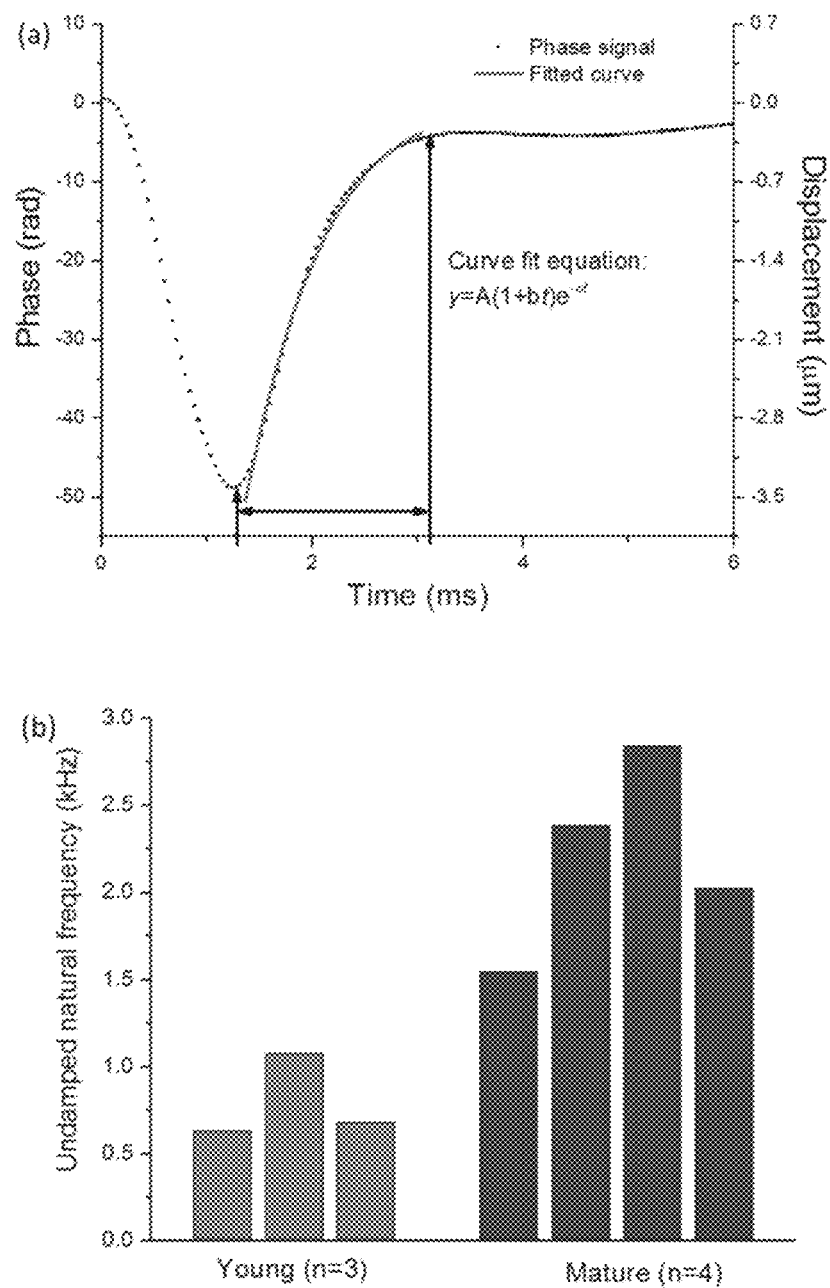
FIG. 8 shows (a) a recovery process fitted by $y(t)=A(1+bt)e^{-\omega t}$ and (b) the natural frequencies $\omega$ for the young (n=3) and mature (n=4) lenses.

The natural frequencies ω=√k/m in the lenses are shown in FIG. 8. The natural frequency was extracted from the relaxation process of the lens surface after the excitation by acoustic radiation force was removed. The natural frequency is associated with the elasticity of the sample. The recovery process in each of the phase profiles was fitted by the model, as shown in FIG. 8(a). During the curve fitting process, it was found that the damping ratio, ξ, was over 0.99, which was approximated to 1 for each eye. Hence, the formula y(t)=A(1+bt)e$^{-\omega t}$ was employed to analyze the relaxation process. In FIG. 8(b), the natural frequency, ω, for the two age groups is compared. The natural frequency values of the young and the mature lenses are 0.8±0.2 kHz and 2.2±0.5 kHz, respectively. The results show that the young lenses had a lower natural frequency than the mature lenses. In addition to the maximum displacements, the natural frequencies demonstrate that the stiffness of the mature lenses is greater than that of the young lenses.

The relaxation process is mainly associated with the viscoelastic properties of the lens. Small oscillations during the recovery process were observed in both the young and mature lenses, as a result of dynamic processes in the lens after the rapidly applied force. It should be noted that there is a high variability in the mature samples for both the elasticity measurements by US-OCE and uniaxial mechanical compression testing. This may imply that the effect of age on the lens elasticity varies between individuals.

Figure 9:
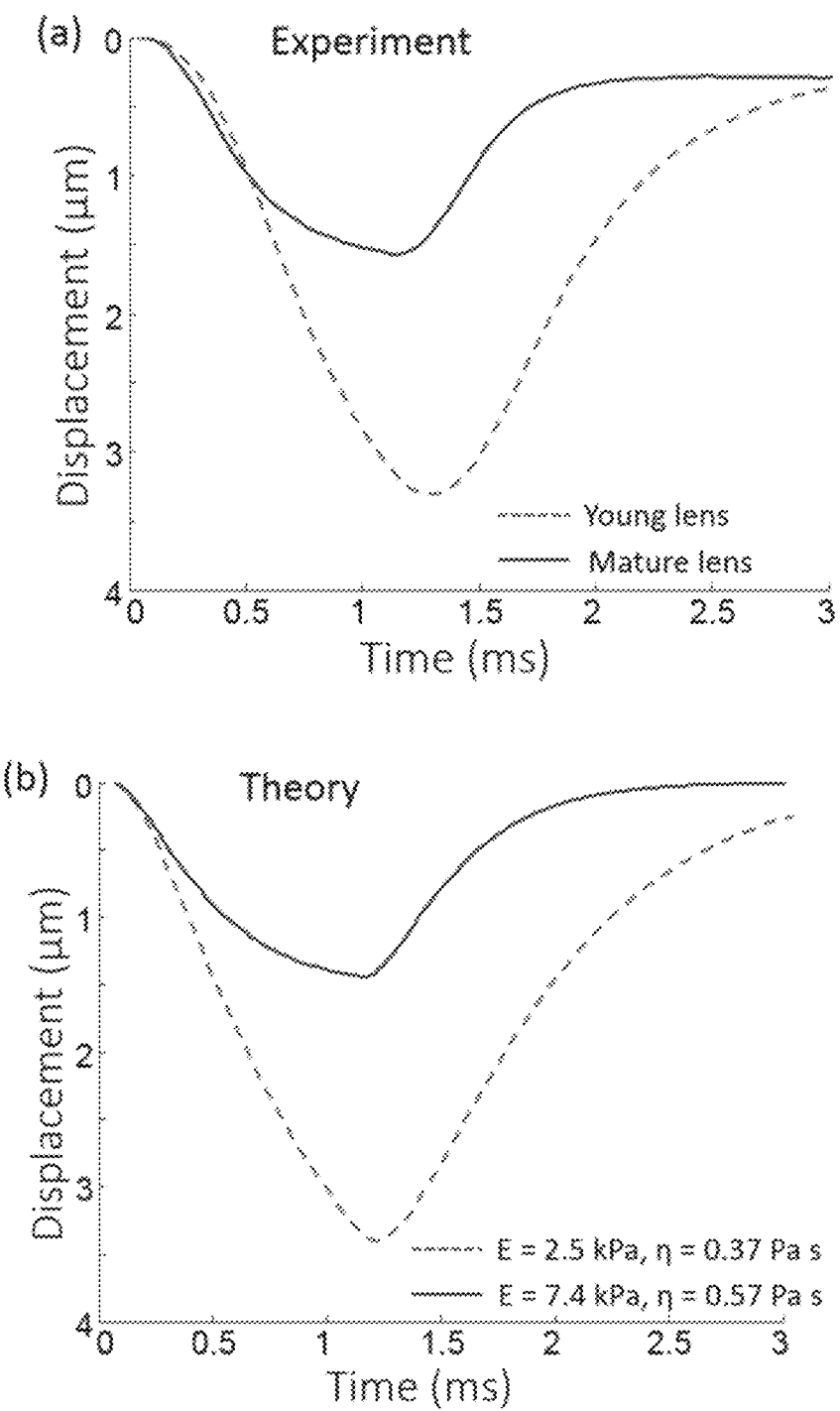
FIG. 9 shows (a) typical experimentally measured and (b) theoretically calculated displacements on the lens surface for young and mature lenses.

Quantitative measurements of the mechanical properties of the crystalline lens based on the US-OCE system required the development of an appropriate mechanical model and reconstructive procedure. A reconstruction based on the model of a homogeneous viscoelastic layer was utilized, as presented above. FIG. 9 presents a comparison of the displacements measured at the surface of young and mature lenses and displacements calculated using the model of a viscoelastic layer with mechanical properties found using the error minimization procedure. Theoretically calculated displacements are calculated for viscoelastic parameters E and $\eta$ obtained after the minimization procedure: E=2.5 kPa and $\eta$=0.37 Pa·s for young lens and E=7.4 kPa and $\eta$=0.57 Pa·s for mature lens. Note, that only time characteristics of the displacements were used and the displacement amplitude was not taken into account. To match theoretical and experimental displacement profiles, the acoustic pressure at the focal point of the ultrasound transducer in theoretical model was 15 Pa for both for young and mature lenses. While the acoustic radiation pressure was not directly measured in experiments, it was likely the same in all experiments regardless of the animal age. Similarly, the amplitude of the surface pressure was assumed the same in theoretical model. Interestingly, the maximum displacement in the young lens was twice the displacement in the mature lens both in the experimental and in theoretical results. However, the reconstruction results show the young lens maximum displacement as three times that of the mature lens. In the mature lens, experimental and theoretical profiles demonstrate saturation of the displacement at the end of the acoustic pulse, which happens where the elastic response of the medium compensated for the acoustic force. These results are in agreement with previous results, where acoustic radiation force was used to move laser-induced microbubbles produced in crystalline lenses. However, the US-OCE method, which combines acoustic radiation force excitation and phase-sensitive OCT measurement, has the advantage of noninvasive detection. In addition, only a minimal acoustic radiation force is required to induce a detectable deformation due to the high displacement sensitivity of phase-resolved OCT detection. This helps to preserve the structural and functional properties of the ocular tissues.

Figure 10:
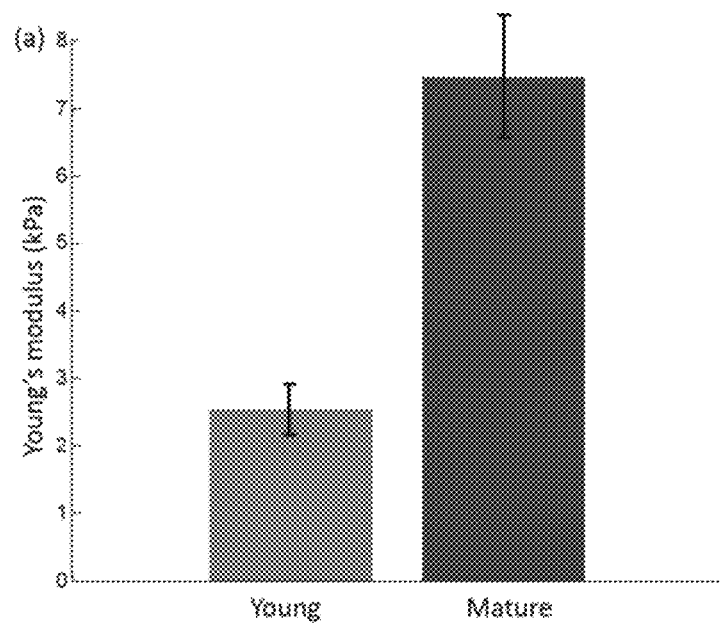
FIG. 10 shows (a) Young's modulus and (b) shear viscosity modulus of young (n=3) and mature (n=4) lenses estimated based on a model of the viscoelastic layer.
Figure 10:
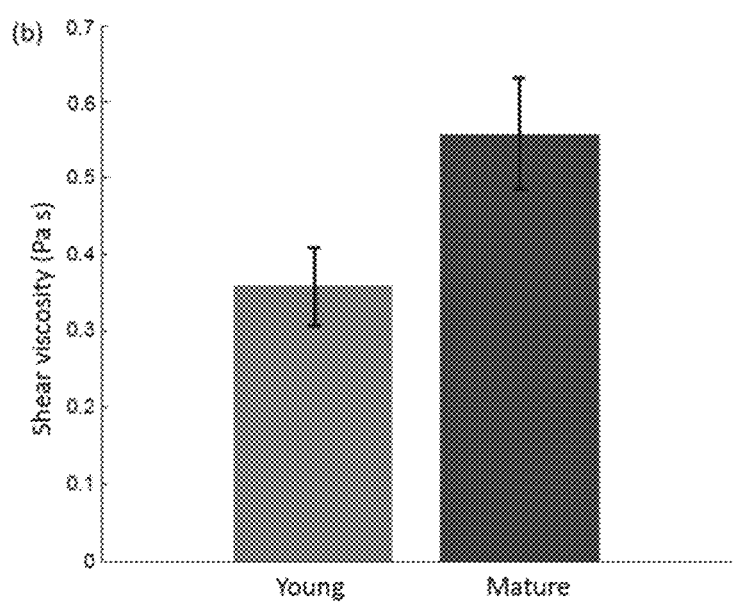

The result of the reconstruction of Young's modulus and shear viscosity for young and mature lenses is shown in FIG. 10. While there was a significant increase in the Young's, the increase of shear viscosity was less pronounced. These results are in agreement with previous results for bovine lenses, where age-related changes in elastic properties were more pronounced than changes in viscous properties.

Figure 11:
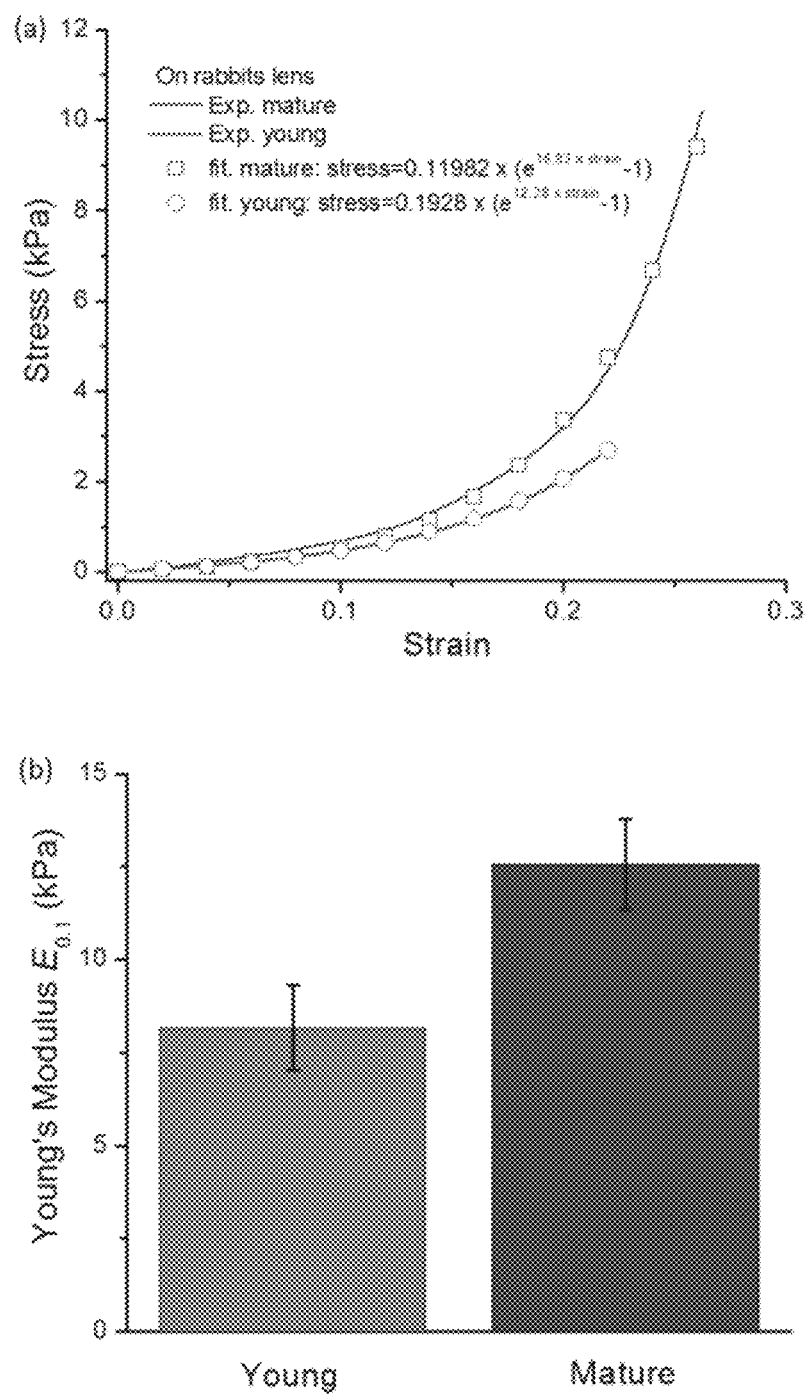
FIG. 11 shows (a) uniaxial mechanical tests and fitted stress-strain curves for typical young and mature rabbit lenses and (b) the distribution of the Young's modulus $E_{0.1}$ at strain $\varepsilon=0.1$ for the young (n=9) and mature (n=4) rabbit lenses.

The stress-strain curves and the Young's moduli of the young and the mature lenses are compared in FIG. 11. FIG. 11($a$) shows typical examples of the stress-strain curves measured on the young and mature rabbit lenses by uniaxial mechanical compression testing. The stress-strain curves for the young and mature lenses can be fitted as stress=0.1928 ($e^{12.28 \times strain}$−1) and stress=0.11892($e^{16.83 \times strain}$−1), respectively. At a strain of 0.1, the Young's moduli of the young (n=9) and mature lenses (n=4) are 8.2±1.1 kPa and 12.6±1.2 kPa, respectively, as shown in FIG. 11($b$). This result clearly shows that the mature lenses are stiffer than the young lenses, confirming the US-OCE results.

As shown in FIG. 9, the results of the model-based calculations are in good agreement with the experimental data. However, the reconstructed Young's modulus values are lower than expected based on the results of uniaxial mechanical compression tests and previous data obtained in bovine lenses. The underestimation in the elastic modulus could be a result of several factors. The presence of the aqueous humor on the displacement of the lens surface was not taken into account, as a free boundary condition on the surface of the lens was assumed. This influence may result in the loss of the acoustic energy and Young's modulus underestimation. In addition, the crystalline lens is an inhomogeneous object, whereas the model used was of a homogeneous layer. Therefore, the reconstruction results may correspond to the cortex of the lens, which is softer than the nucleus. Several other factors, such as the motion of the lens as a whole object, the influence of the lens capsule, and the spatial distribution of acoustic pressure at the focal zone were not considered in the model, but may also be important. Despite these issues, the current method has been demonstrated as a promising tool for noninvasive assessment of changes in the biomechanical properties of the crystalline lens in situ. This method could successfully applied to other methods of excitation as well as other tissues.

What is claimed is:

1. A method for measuring biomechanical properties of tissues and for differentiating tissue samples using optical coherence elastography, comprising:
   inducing elastic waves in the tissue samples;
   detecting properties of the waves using interferometry, low coherence interferometry, or optical coherence tomography at measurement positions along the waves, wherein the measurement positions are the same or different, and wherein detected properties include measured wave velocities, measured wave displacement amplitudes, and measured wave dispersion;
   determining biomechanical properties of the tissue samples by using the detected properties to create elastic wave displacement profiles and performing temporal or spatial analysis of the elastic wave displacement profiles or one or more of the detected properties of the elastic waves;
   differentiating the tissue samples having different elastic wave displacement profiles or one or more different detected properties;
   normalizing the elastic wave displacement profiles for the tissue samples having similar measured wave velocities and needing further differentiation to produce normalized wave displacement data;
   using the normalized wave displacement data to identify tissue samples having faster wave attenuation and slower wave attenuation; and
   classifying the tissue samples having faster wave attenuation as tissue sample having increased viscosity and reduced stiffness and the tissue samples having slower wave attenuation as tissue samples having reduced viscosity and increased stiffness.

2. The method of claim 1, wherein the tissue samples are ocular or any other soft or hard tissue samples.

3. The method of claim 1, wherein the step of inducing elastic waves is by any internal or external methods such as using an ultrasound/air puff/laser pulse delivery subsystem.

4. The method of claim 1, wherein the step of determining biomechanical properties of the tissue samples is by calculating Young's modulus using the detected properties of the elastic waves or the elastic wave displacement profiles.

5. The method of claim 1, wherein the step of normalizing the elastic wave displacement profiles is by dividing the measured wave displacement amplitudes at different measurement positions along the waves by the measured wave displacement amplitude at an excitation position.

6. The method of claim 1, wherein the step of using the normalized wave displacement data to identify tissue samples having faster wave attenuation and slower wave attenuation is by using a customized ratio having a formula of:

$$r_{(ND_1/ND_2)} = \text{mean}(r_i) \pm \text{std}(r_i)$$

wherein $$r_i = \frac{ND_{1i}}{ND_{2i}}$$

and ND1i and ND2i are normalized displacement data at an $i^{th}$ different measurement position for a first and a second tissue sample, wherein if $r_{(ND1/ND2)}$ is significantly greater than 1, the second tissue sample is identified as having faster wave attenuation and the first tissue sample is identified as having slower wave attenuation, and wherein if r is significantly less than 1, the first tissue sample is identified as having faster wave attenuation and the second tissue sample is identified as having slower wave attenuation.

7. The method of claim 6, wherein the step of using the normalized wave displacement data to identify tissue samples having faster wave attenuation and slower wave attenuation is repeated for different tissue samples.

\* \* \* \* \*

UNITED STATES PATENT AND TRADEMARK OFFICE
CERTIFICATE OF CORRECTION

PATENT NO. : 10,405,740 B2
APPLICATION NO. : 15/632657
DATED : September 10, 2019
INVENTOR(S) : Kirill V. Larin et al.

It is certified that error appears in the above-identified patent and that said Letters Patent is hereby corrected as shown below:

In the Specification

1. In Column 11, Line 5, delete "(F)," and insert -- (E), --, therefor.

2. In Column 12, Line 15, delete "d=√6/3D" and insert -- d=√6/3D. --, therefor.

3. In Column 12, Line 20, delete "σ=M($e^{Nϵ}$-1)" and insert -- σ=M($e^{Nϵ}$-1), --, therefor.

Signed and Sealed this
Eighteenth Day of February, 2020

Andrei Iancu
*Director of the United States Patent and Trademark Office*